(12) United States Patent
Marchal

(10) Patent No.: US 7,939,568 B2
(45) Date of Patent: May 10, 2011

(54) USE OF A COMPOSITION COMPRISING VITAMIN K1 OXIDE OR A DERIVATIVE THEREOF FOR THE TREATMENT AND/OR THE PREVENTION OF MAMMAL DERMATOLOGICAL LESIONS

(75) Inventor: Alfred Marchal, Waterloo (BE)

(73) Assignee: Auriga International S.A., Waterloo (BE)

( * ) Notice: Subject to any disclaimer, the term of this patent is extended or adjusted under 35 U.S.C. 154(b) by 0 days.

(21) Appl. No.: 10/542,914

(22) PCT Filed: Jan. 20, 2004

(86) PCT No.: PCT/BE2004/000011
§ 371 (c)(1),
(2), (4) Date: Mar. 7, 2006

(87) PCT Pub. No.: WO2004/064798
PCT Pub. Date: Aug. 5, 2004

(65) Prior Publication Data
US 2006/0154983 A1    Jul. 13, 2006

Related U.S. Application Data

(60) Provisional application No. 60/319,887, filed on Jan. 20, 2003.

(30) Foreign Application Priority Data

Jan. 28, 2003   (EP) .................................... 03447019

(51) Int. Cl.
  *A61K 31/122* (2006.01)
  *A61K 31/12* (2006.01)
  *A61K 7/48* (2006.01)
  *C07C 49/303* (2006.01)
(52) U.S. Cl. ........................................ 514/681; 568/326
(58) Field of Classification Search ........................ None
See application file for complete search history.

(56) References Cited

U.S. PATENT DOCUMENTS

| 3,070,499 | A   | 12/1962  | Mullins et al. |        |
|-----------|-----|----------|----------------|--------|
| 5,945,409 | A * | 8/1999   | Crandall       | 514/78 |
| 5,981,601 | A * | 11/1999  | Nagley et al.  | 514/690 |
| 6,180,136 | B1* | 1/2001   | Larson et al.  | 424/450 |

FOREIGN PATENT DOCUMENTS

| GB | 744376      | 2/1956  |
|----|-------------|---------|
| JP | 05-320039   | 3/1993  |
| WO | WO 94/00135 | 1/1994  |
| WO | WO 97/39746 | 10/1997 |

OTHER PUBLICATIONS

Ryall, R.P., Nandi, D.L., Silverman, R.B., "Substituted Vitamin K Epoxide Analogues. New Competitive Inhibitors and Substrates of Vitamin K1 Epoxide Reductase", J. Med. Chem 1990 (33) 1790-1797.*
Dowd et al. J. Am. Chem. Soc. 1991, 113, 7734-7743.*
Elson, MD, "Topical Phytonadione (Vitamin $K_s$) in the Treatment of Antinic and Traumatic Purpura", Cosmetic Dermatology, vol. 8, No. 12, Dec. 1995, 6 pp. (which consist of 3 cover pages and pp. 25-27).
Lou, MD et al., "Effects of Topical Vitamin K and Retinol on Laser-Induced Purpura on Nonlesional Skin", Dermatol Sug. vol. 25, No. 12, Dec. 1999, pp. 942-944.
Shah, MD et al., "The Effects of Topical Vitamin K on Bruising After Laser Treatment", J Am Acad Dermatol, Aug. 2002, pp. 241-244.

* cited by examiner

*Primary Examiner* — Daniel M Sullivan
*Assistant Examiner* — Yevegeny Valenrod
(74) *Attorney, Agent, or Firm* — Merchant & Gould P.C.

(57) ABSTRACT

The present invention is related to the use of a composition having an adequate pharmaceutical or cosmetic carrier or diluent and a sufficient amount of vitamin K1 oxide or its derivative for the treatment and/or the prevention of mammal dermatological lesions.

The present invention is also related to a cosmetic composition having an adequate cosmetic carrier, phospholipids and vitamin K1 oxide or its derivative.

9 Claims, No Drawings

USE OF A COMPOSITION COMPRISING VITAMIN K1 OXIDE OR A DERIVATIVE THEREOF FOR THE TREATMENT AND/OR THE PREVENTION OF MAMMAL DERMATOLOGICAL LESIONS

FIELD OF THE INVENTION

The present invention is related to the use of a composition comprising vitamin K1 oxide or a derivative thereof for the treatment and/or the prevention of mammal dermatological lesions and to the cosmetic composition comprising vitamin K1 oxide.

BACKGROUND OF THE INVENTION AND STATE OF THE ART

Vitamin K1 (phylloquinone) is needed for proper bone formation and blood clotting, in both cases by helping the body transport calcium. Vitamin K (2-methyl 3-phytyl-1,4-naphtoquinone) and its derivative have already been used in pharmaceutical or cosmetic compositions for their various anti-inflammatory or dermatological applications.

However, the incorporation of vitamin K1 in a cosmetic composition is unstable in certain conditions when exposed to light and UV light and could modify the colour of cream and other vehicles of cosmetic compositions.

The document U.S. Pat. No. 5,510,391 describes a method for treating blood vessel disorders of the skin using vitamin K. Such disorders include actinic and iatrogenic purpura, lentigines, telangiectasias of the face, spider angiomas and spider veins of the face.

The document JP-05320039 describes a cosmetic composition comprising vitamin K1 oxide without specification of any use.

The document WO94/00135 describes the use of a pharmaceutical composition in the treatment of symptoms of chronic inflammatory disorders, said composition comprising at least two pharmaceutically active agents whose combination produces an anti-inflammatory and analgesic effect. Said document also describes that the safety and effectiveness of the product may be optimised by co-administration of vitamins and derivatives thereof. Among the mentioned vitamins are vitamin K1 and vitamin K1 oxide.

The document GB-744 376 describes a stable oily vitamin emulsion comprising an oily vitamin and lecithin dispersed in water. The vitamins could be vitamin A, D, E, K1 or vitamin K1 oxide. Said document also describes that vitamin K1 oxide emulsion is a colourless oil, somewhat more stable than vitamin K1, but having the same physiological activity as vitamin K1 and resulting in a stable emulsion which is not affected by heating at a temperature of 120° C. for two hours period.

The document U.S. Pat. No. 3,070,499 describes a parenteral aqueous solution of fat soluble vitamin wherein the fat soluble substance is vitamin K1 oxide which finds application in nutrition for the prevention and the treatment of certain well known diseases.

AIMS OF THE INVENTION

A first aim of the present invention is to propose a new composition which finds advantageous applications in the treatment of various mammal dermatological lesions, especially human dermatological lesions, and more especially lesions which affect the face, but which does not present the drawbacks of the state of the art.

Another aim of the present invention is to provide such composition which is more stable and which does not present the yellow colour of cream and vehicles already used in the state of the art and which therefore does not render the clothes of the consumer dirty.

A further aim of the present invention is to provide a composition which is not sensitive to light or UV-radiation and which therefore decreases or eliminates side effects such as consumer skin sensitivity or allergy following sun exposure.

A last aim of the present invention is to provide a composition having a similar or an improved activity (including an enhanced penetration through the skin and an excellent moisture-binding capacity) in view of the known composition of the state of the art.

SUMMARY OF THE INVENTION

A first aspect of the present invention is related to the use of a composition comprising vitamin K1 oxide or a derivative thereof and an adequate carrier for the treatment and/or the prevention of mammal (including human) dermatological lesions, selected from the group consisting of bruises (possibly associated with cosmetic surgery), vascular disorders of the skin such as small broken vessels, spider veins, varicoses, blotches on the face, any purpura on the face, body and legs (including actinic purpura and post laser skin treatment purpura), irritation of the skin following chemical peel, Shambourg's disease and a mixture thereof.

Advantageously, the use of the composition according to the invention also presents other advantageous associated therapeutical effects when applied upon dermatological lesions, such as topical anti-inflammatory effects upon the human skin.

Preferably, the composition used according to the invention is either in the form of a pharmaceutical composition or a cosmetic composition comprising an adequate pharmaceutical or cosmetic carrier or diluent.

Advantageously, the cosmetic composition further comprises a sufficient amount of a penetrating agent such as phospholipids, preferably said penetrating agent is in the form of nanosomes, described hereafter.

Examples of a cosmetic composition could be in the form of a cream, a gel, a lotion and/or a liquid.

The vitamin K1 oxide present in the composition has the following formula (I) derivative:

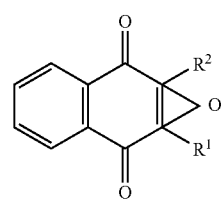

wherein R1 is an alkyl group, preferably an alkyl chain comprising between 3 and 20 carbons, preferably an alkyl chain of 12 carbons, possibly branched, more preferably of fomula (II).

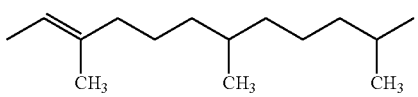

and wherein R2 is H or an alkyl group, preferably a ethyl or a methyl group.

Advantageously, the vitamin present in the composition has the formula I wherein R1 is of formula II and R2 is a methyl group (vitamin K1 oxyde).

Advantageously, in the composition according to the invention, the compound of the invention (vitamin K1 oxide or its derivative) is present in nano-sized lipidic particles (hereafter called nanosomes), preferably lipidic particles having a diameter comprised between about 50 and about 400 nanometers, more preferably between about 100 and about 350 nanometers, between about 120 and about 300 nanometers, between about 155 nanometers and about 200 nanometers, more preferably about 180 nanometers (±30 nanometers).

The stability of the lipidic nanosome is obtained with particles having a suitable dimension of about 180 nanometers and more than 80% (preferably all) of the nanosomes of the composition should reach the same size of about 180 nanometers. If it happens that a difference in such size exceeds 30%, then a fusion process will occur meaning the formation of greater nanosomes that will become instable and further will destroyed themselves by breaking. It results in a possible dispersion of the compound (vitamin K1 oxide or its derivative) and the lipidic membrane and loose of the nanosome advantages.

Advantageously, the extend structure of the nanosome has the same physico-chemical properties that the cell membrane and therefore, the nanosome is able to penetrate easily and quickly the skin and improve the cosmetic and therapeutic properties of the compound (vitamin K1 oxide or its derivative). Furthermore, the integration of the compound (vitamin K1 oxide or its derivative) in nanosomes will enhance therapeutical and cosmetical efficacy while using less substance.

The nanosomes are made of single or multi-lipidic layers of phospholipids, preferably of phosphatidylcholine. Preferably, the nanosomes are single lipidic monolayers of phospholipids, preferably of phosphatidylcholine.

In the composition according to the invention, the compound (vitamin K1 oxide or its derivative) is present in a sufficient amount to treat or reduce the effect of the abovementioned dermatological lesions. Preferably, said sufficient amount is comprised between 0.5% wt and about 10% wt of the total composition, preferably about 5% wt of the total composition (the total % wt of the composition being 100%).

The composition according to the invention advantageously comprises other efficient cosmetic or pharmaceutical compounds, such as other vitamins (which could be present in nanosomes, preferably having the same size as the ones which include vitamin K1 oxide or its derivative). Preferred vitamins are vitamin A, vitamin C and vitamin E which present advantageously a synergic activity with vitamin K1 oxide or its derivative. Vitamins C and E are able to maintain iron under a bivalent form (ferrous) avoiding transformation to trivalent form (ferric).

In the composition according to the invention, the vitamin A (pure retinol) could be in the form of ester of vitamin A which is more stable for a cosmetic use. With the use of ester derivatives, the efficacy is reduced.

Furthermore, when using in eyes area, a possible irritating side effect of retinol could be obtained, especially when the cosmetic composition is used for a long period of time. Therefore, retinol is preferably introduced into polymer system of micro particles that deliver the retinol slowly through the stratum corneum, only when the product is applied directly on the skin. The polymer sphere will remain on the surface of the skin. In order to reduce a possible soft light effect with barium sulphate, mica and titanium dioxide (this mineral can not penetrate the skin and shows a change in the common light with a dulled effect), the concentration of said compound could be reduce in the cosmetic composition according to the invention, especially if the treatment should take several months.

Other active ingredients are ingredients which improve the vitamin activity, preferably said compounds are selected from the group consisting of the following elements with the following preferred (wt) %: phytonadione (about 0.5 to about 2%), tocopheryl acetate (about 1%), ascorbic palmitate (about 0.5%), retinyl palmitate (about 0.5%) and tocopherol (about 0.2%).

Other advantageous compounds comprised in the composition (a cosmetic composition of the invention) are: aqua (solvent), retinol, propylene glycol (moistening element), triethanolamin (neutralizing element), lecithin (improves hydratation), carbomer (thickening element), ethoxydiglycol (penetration agent), some specific lipids, such as phospholipids (penetration agents), EDTA (complexing agent), C12-C15 alkyl benzoate, caprylic capric triglycerides, parafinum liquidum, cyclomethicone, glycerine, sodium PCA, mica, barium sulfate, titanium dioxide, polysorbate 20, acrylate copolymer, phenoxyethanol, acrylate C10-C30, alkyl crosspolymer, propyl paraben, menthyl paraben, alcohol (conservative), propylene glycol (moistening agent), BHT or BHA (antioxidants), . . . .

The phospholipids used in the present invention improve the skin penetration of vitamins, especially vitamin K1 oxide or its derivative and vitamin A.

The present invention will be described in more details in the following examples, presented as a non-limited illustration of preferred embodiment of the present invention.

EXAMPLE 1

Protocol for Bruises

For the purpose of the study, three compositions (cream cosmetic compositions) have been used in various vehicles with different concentrations in vitamin K1 and vitamin K1 oxide. The study was conducted in double blind on 12 human volunteers (six males and six females). The purpose of the study was to show a better or at least a similar activity of vitamin K1 oxide versus vitamin K1 in resolution of bruises.

The 12 human volunteers previously received information on the goal and the course of the trial. Four ecchymoses have been induced on each patient (2 on each forearms) and the efficacy of each cream cosmetic composition has been evaluated by observation of time reduction of each ecchymosis. Each patient was examined every day and pictures have been taken at the same time. No other cream was applied and the patients were not allowed to take any other medication (no aspirin, no anti-inflammatory active compound). The creams were applied twice a day.

Materials and Method

The table 1 presents 4 different creams and their contents.

TABLE 1

| Creams | |
|---|---|
| cream 1 | 5% free vitamin K1 cream |
| cream 2 | 2% vitamin K1 gel (nanosome particles) |
| cream 3 | 5% vitamin K1 oxide cream |
| cream 4 | No treatment as witness |

The following quantitative results in days of reduction of bruises are presented in the following table 2 and show the advantageous effects of vitamin K1 oxide compared to vitamin K1 upon different patients.

TABLE 2

| Patient | Cream 1 5% Vitamin K1 | Cream 2 2% Vitamin K1 nanosome particles | Cream 3 5% Vitamin K1 Oxide | Cream 4 No treatment |
|---|---|---|---|---|
| A1 | 11 | 9 | 11 | 10 |
| A2 | 11 | 8 | 10 | 11 |
| A3 | 13 | 10 | 10 | 13 |
| A4 | 10 | 11 | 13 | 13 |
| A5 | 11 | 11 | 9 | 14 |
| A6 | 13 | 11 | 11 | 13 |
| B1 | 12 | 9 | 10 | 12 |
| B2 | 12 | 11 | 11 | 13 |
| B3 | 13 | 11 | 10 | 12 |
| B4 | 12 | 10 | 10 | 13 |
| B5 | 12 | 12 | 10 | 13 |
| B6 | 12 | 11 | 9 | 11 |
| Total | 142 | 124 | 124 | 148 |
| Mean | 11.83 | 10.33 | 10.33 | 12.33 |

EXAMPLE 2

Protocol for Spider Veins

The same study was performed on 10 human patients presenting spider veins or small broken blood vessels on legs and face.

The treatment was done during four weeks with two applications of the creams per day.

The group vitamin Oxide shows the best results compared to other formulation comprising vitamin K1.

The composition (a cosmetic composition according to the invention) may be applied thinly twice a day, morning and evening, after cleansing of the skin; gently massage into skin and till the gel is absorbed, is preferred.

The composition according to the invention is recommended for use for 10 to 15 days as preparatory skin care before and after surgical and medical cosmetic procedure.

The composition according to the invention should preferably be applied before all other beauty or cosmetic skin care products and can be used as a base for those preparations; said composition should not be applied directly upon wounds, mucus areas or eyes due to some hypersensitivity.

The improved stability of vitamin K1 oxide compared to vitamin K1, reduces also unexpectedly the side effects of a cosmetic composition. The inventors have observed that in presence of light (and possibly improved with the addition of vitamin A), vitamin K1 is transformed into Menadione (vitamin K3) and 1.4.Naphtoquinone that induces allergic side effects. Such transformation of vitamin K1 oxide is not observed in the presence of light and these side effects are not present when the cosmetic composition according to the invention is applied upon mammal skin.

Furthermore, contrary to vitamin K1, the mixing of vitamin K1 oxide and retinol (or retinol palmitate) does not allow the formation of chromophoric group.

The introduction of active ingredients, especially vitamin K1 oxide and its derivative, in nanosomes improves advantageously penetration and absorption of vitamins, reduces the concentration of vitamins required and provides a system release of vitamins for about 12 hours and therefore reduces the cost of the composition compared to the compositions of the state of the art.

The invention claimed is:

1. A method for treatment of dermatological lesions of a mammal comprising:
submitting a dermatological lesion to a composition comprising a sufficient amount of a compound formula I

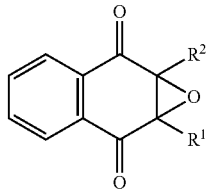

wherein R1 is:

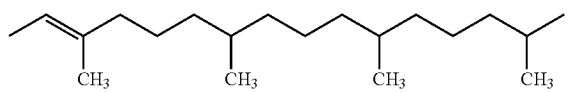

and wherein R2 is methyl, in a pharmaceutical or cosmetic carrier.

2. The method of claim 1, wherein the lesion is selected from the group consisting of bruises, vascular disorder on the skin, spider veins, varicoses, blotches on the face, purpura on the face body or legs, irritation following use of chemical peel, Schamberg's disease or a mixture thereof.

3. The method of claim 1, wherein the compound is present in nano-sized lipidic particles, comprised between about 50 and about 400 nanometers in diameter.

4. The method of claim 3, wherein the nano-sized lipidic particles have a diameter of about 180 nanometer.

5. The method of claim 3, wherein the nano-sized lipidic particles are made of phospholipid layers.

6. The method of claim 1, wherein the composition is a cosmetic composition comprising a sufficient amount of the compound and an adequate cosmetic carrier.

7. The method of claim 6, wherein the sufficient amount of the compound is comprised between about 0.5% wt and about 10% wt of the composition.

8. The method of claim 6, wherein the cosmetic composition is in the form of a cream, a gel, a lotion or a liquid.

9. The method according to claim 6, wherein the composition further comprised other vitamins, preferably vitamins selected from the group consisting of vitamin A, vitamin C, vitamin E or a mixture thereof.

* * * * *